United States Patent [19]
Silver et al.

[11] Patent Number: 5,827,217
[45] Date of Patent: Oct. 27, 1998

[54] PROCESS AND APPARATUS FOR HARVESTING TISSUE FOR PROCESSING TISSUE AND PROCESS AND APPARATUS FOR RE-INJECTING PROCESSED TISSUE

[76] Inventors: Frederick H. Silver, 103 Springbrook Dr., Bangor, Pa. 18013; Ary S. Chernomorsky, 40 Averell Dr., Morris Plains, N.J. 07950

[21] Appl. No.: 708,307
[22] Filed: Sep. 4, 1996
[51] Int. Cl.⁶ .................................................. A61B 17/00
[52] U.S. Cl. .............................................. 604/28; 606/131
[58] Field of Search .................... 606/1, 184–187, 606/131–133; 604/28; 623/15; 435/1; 128/749–755

[56] References Cited

U.S. PATENT DOCUMENTS

| | | | |
|---|---|---|---|
| 4,604,346 | 8/1986 | Bell et al. | 606/132 |
| 4,817,631 | 4/1989 | Schnepp-Pesch et al. | 128/753 |
| 4,982,739 | 1/1991 | Hemstreet et al. | 128/753 |
| 4,986,278 | 1/1991 | Ravid et al. | 128/753 |
| 5,336,616 | 8/1994 | Livesey et al. | 623/15 |
| 5,546,957 | 8/1996 | Heske | 128/749 |

*Primary Examiner*—Michael Powell Buiz
*Assistant Examiner*—William Lewis
*Attorney, Agent, or Firm*—Louis E. Marn

[57] ABSTRACT

There is disclosed a method and apparatus for harvesting tissue using a cannula having a diameter of from 0.5 to 4.0 mm and of a length of from 25 to 20 cm to access by minimally invasive techniques a host to withdraw autogenous tissue processed to remove loose fat and/or fragmented tissue. Thereafter, the resulting tissue substrate is morcellated to form particulate tissue of a particle size of from 1 to 200 $\mu$m. The particulate material is thence passed through screens having opening sizes of from 1 to 100 $\mu$m to form a material of a size for introduction into a syringe of from 16 to 30 gauge for implantation in the host. The processed tissue may be admixed with extenders, gelling agents and the like.

8 Claims, 1 Drawing Sheet

PROCESS AND APPARATUS FOR HARVESTING TISSUE FOR PROCESSING TISSUE AND PROCESS AND APPARATUS FOR RE-INJECTING PROCESSED TISSUE

BACKGROUND OF THE INVENTION

1. Field of the Invention

This invention relates to a process and apparatus for harvesting tissue for processing tissue and process and apparatus for re-injecting process tissue.

2. Description of the Prior Art

It is known to harvest tissue from one part of a body and transplanted same to another part of the body to correct genetic and acquired defects. Tissue is harvested using cutting devices designed to form sheets of material, such as skin or drilling devices to create plugs, such as bone. A major drawback to the use of harvested tissue obtained with cutting or drilling devices is that the graft material obtained from such processes has to be harvested with dimensions that exactly fit the defect to be filled. Additionally, the material must be either meshed in the case of a skin graft or trimmed in the case of a bone graft to fit into the defect. Such drawbacks limit the use of harvested tissues to defects that can be filled with the available harvested material or that can be accessed in an open surgical field.

There are various methods and apparatus for cutting and removal of tissues from mammals; however, each of such methods and apparatus suffer from one or more deficiencies. For example, in U.S. Pat. No. 4,265,231, there is illustrated a cannula attached to an adaptor connected to a drill for making passageway through the bone; however, there is no description as to how the bone material can be collected and processed. In U.S. Pat. No. 4,541,423, there is illustrated an apparatus for drilling a curved hole having a flexible shaft; however, again, no removal and processing of cut bone or tissue. U.S. Pat. Nos. 4,589,141; 4,603,694; 4,751,922; and 4,832,683 also illustrate an apparatus or process for removal; however, no processing of tissue is disclosed. In U.S. Pat. No. 5,269,785, there is illustrated a percutaneous removal apparatus having a flexible drilling shaft with a cutting tip mounted on the shaft, a power source for transmitting the shaft and the container for collecting one or more components of harvested tissue is disclosed and wherein the harvested tissue fragments are subsequently implanted using surgical techniques.

OBJECTS OF THE INVENTION

An object of the present invention is to provide an improved process and apparatus for harvesting soft and hard tissue.

Another object of the present invention is to provide an improved process and apparatus for harvesting soft and hard tissue to obtain extra cellular matrix for use as graft materials.

Still another object of the present invention is to provide an improved process and apparatus for harvesting soft and hard tissue to obtain viable cells for transplantation.

A still further object of the present invention is to provide an improved process for harvesting soft and hard tissue wherein the harvested tissue is processed for introduction into the host donor by injection through a needle.

SUMMARY OF THE INVENTION

These and other objects of the present invention are achieved by a process and apparatus for harvesting tissue using a cannula having a diameter of from 0.5 to 4.0 mm and of a length of from 25 to 20 cm to access by minimally invasive techniques a host to withdraw tissue to be processed to remove loose fat and/or fragmented tissue. Thereafter, the resulting tissue substrate is morcellated to form particulate tissue of a particle size of from 1 to 200 $\mu$m. The particulate material is thence passed through screens having opening sizes of from 1 to 100 $\mu$m to form a material of a size for introduction into a syringe of from 16 to 30 gauge for implantation in the donor host. The processed tissue may be admixed with extenders, gelling agents and the like.

BRIEF DESCRIPTION OF THE DRAWINGS

These and other objects of the present invention will be readily appreciated by reference to the following detailed description when taken with the accompanying drawings wherein like numerals designate like parts.

DETAILED DESCRIPTION OF THE INVENTION

In the present application, the terms used have the following meaning:

"Autogenous tissue" means transferring a tissue or part of an organ by transferring it into a new position in the body of the same individual.

"Allograft tissue" means tissue obtained from another individual of the same species.

"Implant" means material either solid or liquid used to fill a tissue defect or augment a defect.

"Chemically-modified autogenous tissue" means any autogenous tissue that has been modified by exposure to a solvent or condition that results in the formation of covalent bonds.

"Connective tissue" means any soft or hard tissue containing one or more of the following compounds selected from the group consisting of collagen, proteoglycans, elastic tissue, structural glycoproteins and cells.

Figure 1:
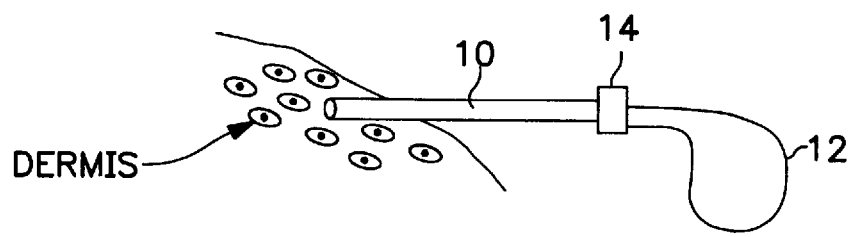
FIG. 1 is a schematic illustration of the assembly for harvesting tissue from a host.
Figure 2:
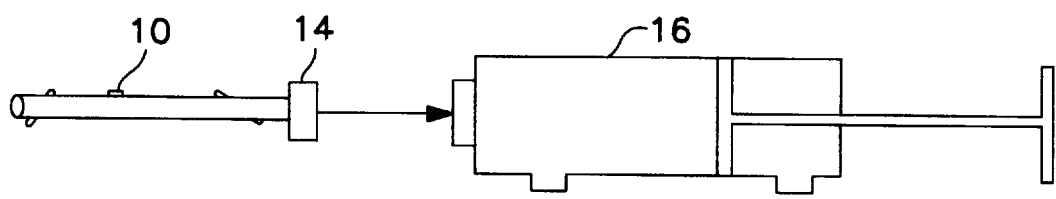
FIG. 2 is a schematic illustration of collecting harvested tissue.

In accordance with one embodiment of the present invention, there is provided a minimally invasive method for harvesting soft and hard tissues. Accordingly, referring to FIG. 1, a cannula 10 having a diameter of from about 0.5 to 4.0 mm and a length of from about 2.5 to 20 cm is introduced into the host subject from which tissue is to be withdrawn for processing to autogenous tissue. After filling of the cannula 10 using a detachable motion control unit 12 connected by an adaptor 14, the tissue is withdrawn from the cannula 10 into a process unit 16, referring to FIG. 2. The tissue is thereafter introduced into a processing vessel (not shown) and contacted with a physiological amount of saline or phosphate buffer to remove any loose fat or fragmented tissue.

The thus partially treated tissue is then fragmented by morcellation in a processing unit using a spinning blade wherein the blade rotates at from 100 to 10,000 RPM's and subjected for processing time period of between 20 seconds to 5 minutes until the partially treated tissue is uniformly fragmented into pieces with an average particle size of from 1 to 200 μm. The thus fragmented tissue is passed through a screen mesh having openings of from 1 to 100 μm until there is collected a material of uniform consistency. The thus processed tissue is introduced into a syringe and thereafter introduced as a graft material by injection into soft or hard tissue defects through a needle of the syringe having an opening of from 16 to 30 gauge.

In another embodiment of the present invention, 1.0 to 10 ml of harvested soft tissue from one site is mixed with from 1.0 to 10 ml of harvested tissue from another site and introduced into the process vessel and contacted with physiologic saline or phosphate buffers to remove loose fat or fragmented tissue. The thus treated mixture is morcellated as hereinabove discussed for a period of from 3 seconds to 5 minutes to form a uniform mixture to be injected by a syringe.

In still another embodiment of the present invention, 1.0 to 10 ml of harvested tissue is introduced into the processing unit and contacted with physiologic saline or phosphate buffers to remove loose fat or fragmented tissues. Thereafter, of from 1.0 to 100 ml of an extender: such as albumin, collagen, gelatin; synthetic polymers, such as poly(lactic) acid; and plant polymers, such as cellulose is admixed with the processed tissue. In addition to such extenders, other physiologic extenders may be added including saline, blood components, concentrated blood components, thrombin, phosphate buffered saline, growth factors and hormones.

In still further embodiment of the present invention, other tissue components, such as blood components, may be admixed with the process autogenous tissue to form a gel, such as by admixing 0.1 to 3.0 ml of concentrated fibrinogen solution with of from 1.0 to 3.0 ml of processed soft or hard tissue. The mixture is permitted to gel with from 10 to 1000 units per ml of thrombin. Additionally, other gelling agents, such as alginates and tissue adhesives can be used to form the solid gelled graft materials.

Figure 3:
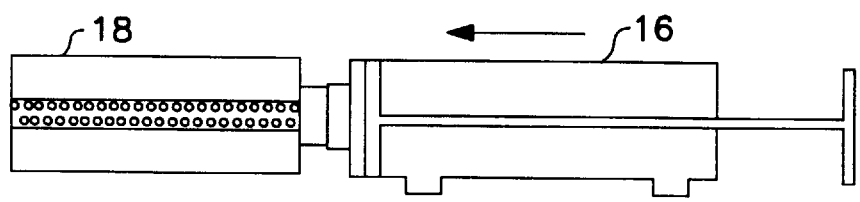
FIG. 3 is a schematic illustration of forming solid substrate.

In still another embodiment of the present invention, the processed soft or hard tissue is formed into autogenous implants in solid form used to repair soft and hard tissue. Accordingly, 1.0 to 3.0 ml of processed tissue is admixed with 1.0 to 3.0 ml of concentrated fibrinogen solution and 10 to 1,000 units per ml of thrombin. The resultant mixture in the process unit 16 is introduced into a mold 18 of predetermined size of from, for example, 1.0 to 10 cm in length referring now to FIG. 3. The gelled tissue is permitted to incubate at 20 to 100% relative humidity at temperatures between about 20° to 30° C. for between 5 to 60 mins.

In accordance with the present invention, the implant material does not stimulate an immune response and persist at the site of implantation. For example, 0.1 to 1.0 ml of harvested and processed tissue may be injected through a needle having a diameter of 16 to 30 gauge into the dermis with no concomitant associated inflammation with the results persisting for from 6 months to 10 years depending on the implantation site.

Figure 4:
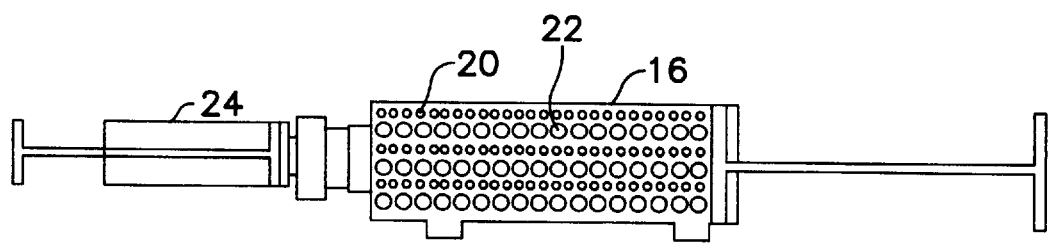
FIG. 4 is a schematic illustration of loading autogenous material for injection into the host.

FIG. 4 illustrates the introduction of extended harvest material 20 together with extended material 22 being introduced into a syringe 24 from the process unit 16.

EXAMPLES OF THE INVENTION

The following examples are illustrative of an apparatus of the present invention, and it is understood that the scope of the invention is not to be limited thereby.

Example 1

The cannula having a hollow shaft of a diameter of 2.0 mm is inserted into a 2.0 mm incision made in the skin and inserted into the dermis above the fat layer. One ml of dermis is removed and the tissue is placed in a processing unit for morcellation for a period of 5 minutes. The morcellated tissue is collected in a 5.0 mm syringe and passed through a series of mesh screens beginning with 100 micrometers down to 0.5 micrometers until the resulting material easily passes through an 18 gauge needle.

Example 2

One ml of dermis is harvested as described in Example 1 and admixed with 1.0 ml of physiological saline (0.9% W/V sodium chloride). The mixture is morcellated as described in Example 1 until the morcellated tissue easily passed through an 18 gauge needle.

Example 3

Ten ml of blood is collected from a host in a sealed sterile tube containing sodium citrate providing a final citrate concentration of 1% (W/V). The blood sample is centrifuged at 600 g for 20 min. and plasma removed with a sterile syringe and transferred to another sterile sealed tube. The plasma is then frozen at −15° C. for 24 hours and thawed at 4° C. Thereafter, the thawed plasma is centrifuged for 5 min. at 3000 g. The supernatant is discarded and the resulting solid material re-solubilized in 1.0 ml of distilled water. The resolubilized material is admixed with 1.0 ml of processed tissue as discussed in Example 1 together with 200 units of bovine thrombin. The resulting mixture is placed on a flat surface and allowed to form a sheet of 200 micrometer in diameter and incubated at room temperature for 10 min.

Example 4

A processed dermis as described in Examples 1 and 2 is injected into depressed skin areas using a 2.0 ml syringe with an 18 gauge needle. The depressed areas are overcorrected by introducing sufficient graft material to elevate the defect area beyond the height of the surrounding skin.

The graft materials of the present invention overcome many of the difficulties in the prior art and have a combination of advantageous new properties. The autogenous tissue is biocompatible and persistent, and does not require skin testing as is necessary with the use of processed animal collagen. Still further, carefully processed harvested tissue results in maintaining of cell viability for successful implantation.

The filler materials described in the present invention overcome many of the problems associated with the use of foreign materials as well as tissue cultured materials. More significant materials of the present invention may be processed during an operation or medical procedure or prepared and then stored for use at a future time. The filler materials include both cells as well as components of connective tissue, and the product is persistent when implanted and as hereinabove discussed. The process of the present invention permits harvesting autogenous tissue, extension and processing of such tissue in the operating room or an outpatient facility or a surgi-center in order to be able to immediately re-introduce the material into the host as an injectable or solid state filler.

The autogenous process tissue of the present invention are especially well suited for the repair of soft tissue injuries as distinguished from prior attempts using autogenous tissues requiring lengthy processing which modifies the chemistry of the connective tissue macromolecules or devitalizes the cellular components.

While the invention herein has been described in connection with an exemplary embodiment thereof, it will be understood that many modifications will be apparent to those of ordinary skill in the art and that this application is intended to cover any adaptations or variations thereof. Therefore, it is manifestly intended that this invention be only limited by the claims and the equivalents thereof.

What is claimed:

1. A process for harvesting tissue, which comprises:
   a.) effecting an incision in a host;
   b.) introducing a cannula having a diameter of about 0.5 to 4.0 mm and a length of from about 2.5 to 20 cm;
   c.) withdrawing a tissue substrate from the host;
   d.) admixing a buffer with said tissue substrate;
   e.) removing loose fat or fragmental tissue from the admixture of step d to form processed tissue;
   f.) morcellating the processed tissue of step e; and
   g.) comminuting the morcellated processed tissue of step f.

2. The process for treating a tissue substrate as defined in claim 1 wherein step f is effected at rotational blade speeds of from 100 to 10,000 RPM's.

3. The process for treating a tissue substrate as defined in claim 2 wherein morcellation is effected for a period of time of from 20 seconds to 5 minutes.

4. The process or treating a tissue substrate as defined in claim 1 wherein comminuting of step g results in a tissue substrate of a particle size for introduction into a syringe of 16 to 30 gauge.

5. A process for introducing autogenous tissue into a host donor of a tissue substrate which comprises the steps of:
   a) admixing a buffer with said tissue substrate;
   b) removing loose fat or fragmented tissue from the admixture of step a);
   c) morcellating the resulting tissue of step b);
   d) comminuting the morcellated tissue of step c); and
   e) introducing into said host donor the comminuted morcellated tissue of step d).

6. The process for introducing autogenous tissue into a host donor as defined in claim 5 wherein step d) is effected to form comminuted morcellated tissue of a particle size for introduction into a syringe of 16 to 30 gauge.

7. The process for introducing autogenous tissue into a host donor as defined in claim 5 wherein step c) is effected at rotational blade speeds of from 100 to 10,000 RPM's.

8. The process for introducing autogenous tissue into a host donor as defined in claim 5 wherein step e) is effected for a period of time of from 20 seconds to 5 minutes.

* * * * *